United States Patent
Ward et al.

(10) Patent No.: US 7,118,534 B2
(45) Date of Patent: Oct. 10, 2006

(54) METHODS FOR MONITORING AND OPTIMIZING CENTRAL VENOUS PRESSURE AND INTRAVASCULAR VOLUME

(75) Inventors: Kevin R. Ward, Glenn Allen, VA (US); Robert W. Barbee, Richmond, VA (US); Rao R. Ivatury, Richmond, VA (US); Bruce D. Spiess, Manakin-Sabot, VA (US); James A. Arrowood, Richmond, VA (US)

(73) Assignee: Virginia Commonwealth University, Richmond, VA (US)

(*) Notice: Subject to any disclaimer, the term of this patent is extended or adjusted under 35 U.S.C. 154(b) by 672 days.

(21) Appl. No.: 10/380,347

(22) PCT Filed: Sep. 21, 2001

(86) PCT No.: PCT/US01/29582

§ 371 (c)(1),
(2), (4) Date: Mar. 13, 2003

(87) PCT Pub. No.: WO02/24053

PCT Pub. Date: Mar. 28, 2002

(65) Prior Publication Data

US 2004/0044290 A1    Mar. 4, 2004

(51) Int. Cl.
*A61B 5/02* (2006.01)
(52) U.S. Cl. ............ 600/490; 600/500; 600/485
(58) Field of Classification Search ............ None
See application file for complete search history.

(56) References Cited

U.S. PATENT DOCUMENTS

| | | | |
|---|---|---|---|
| 4,169,463 A | 10/1979 | Piquard | |
| 4,566,462 A | 1/1986 | Janssen | |
| 5,040,540 A | 8/1991 | Sackner | |
| 5,297,556 A * | 3/1994 | Shankar | 600/481 |
| 5,343,868 A | 9/1994 | Kurscheidt et al. | |
| 5,447,161 A | 9/1995 | Blazek et al. | |
| 5,718,232 A * | 2/1998 | Raines et al. | 600/507 |
| 5,904,143 A | 5/1999 | Magidson et al. | |
| 6,027,452 A * | 2/2000 | Flaherty et al. | 600/485 |
| 6,120,459 A | 9/2000 | Nitzan et al. | |
| 6,749,567 B1 | 6/2004 | Davis et al. | |

* cited by examiner

*Primary Examiner*—Robert L. Nasser
(74) *Attorney, Agent, or Firm*—Whitham, Curtis, Christofferson & Cook, PC

(57) ABSTRACT

Central Venous Pressure (CVP) is non-invasively determined with accuracy comparable to invasive measurement techniques. To do so, curves are plotted based on non-invasively determined patient information obtained by applying a controllable variable (pressure) to a vein of interest at a non-distal point and taking certain measurements (such as pressure and volume measurements) from the patient. An example of a controllable variable is voltage applied in incremental inflation/deflation of a vascular cuff (1). A curve is plotted based on datapoints (such as a volume increase curve or a volume decline curve). Pertinent, accurate CVP and/or blood volume information is obtained from the slope of the non-invasive-based curve. Accurate CVP information is provided without the risks and disadvantages of invasive measurements.

33 Claims, 14 Drawing Sheets

METHODS FOR MONITORING AND OPTIMIZING CENTRAL VENOUS PRESSURE AND INTRAVASCULAR VOLUME

BACKGROUND OF THE INVENTION

1. Field of the Invention

The invention is generally related to medicine. In particular, the invention relates to intravascular volume and central venous pressure (CVP) measurement.

2. Background Description

Manipulation of intravascular volume (i.e., the volume of blood within blood vessels) is an important tool in the treatment of many disease states including but not limited to dehydration, congestive heart failure, renal failure, cardiogenic shock, traumatic and hemorrhagic shock, and septic shock in both their compensated and uncompensated states. However, the physical examination and medical history of a patient have not been demonstrated to produce accurate assessments of a patient's intravascular volume status. A. F. Connors, Jr., N. V Dawson, P K Shaw, H D Montenegro, A R Nara, L Martin, "Hemodynamic status in critically ill patients with and without acute heart disease," Chest, 98(5): 1200–6 (1990); N V Dawson, A F Connors, Jr., T Speroff, A Kenika, P Shaw, H R Arkes, "Hemodynamic assessment in managing the critically ill: is physician confidence warranted," Med Decis Making, 13(3):258–66 (1993); D J Cook, "Clinical assessment of central venous pressure in the critically ill," Am J Med Sci, 299(3):175–8 (1990); D J Cook, D L Simel, "The Rational Clinical Examination. Does this patient have abnormal central venous pressure?" Jama, 275(8):630–4 (1996); M R Shah, V Hasselblad, S S Stinnett, M Gheorghiade, K Swedberg, R M Califf, et al., "Hemodynamic profiles of advanced heart failure: Association with clinical characteristics and long-term outcomes," J Card Fail, 7(2):105–13 (2001).

Normally, the rate of venous return to the heart equals the rate of blood pumped out of the heart and the amount of blood pumped by the right ventricle equals the amount of blood pumped by the left ventricle. A well-known relationship exists between intravascular volume and heart function based on the Frank-Starling law. A Guyton, "Heart muscle: The heart as a pump," in A. Guyton, editor, Textbook of Medical Physiology ($6^{th}$ ed., Philadelphia: W. B. Saunders) (1981), pp. 150–64; A Guyton, "Cardiac output, venous return, and their regulation," in A. Guyton (editor), Textbook of Medical Physiology, id., pp. 274–88. This principle states that within physiologic limits, the heart will pump whatever amount of blood enters the right atrium and will do so without excessive backup of blood or fluid in the veins or tissues.

When excessive central intravascular volume exists it can either be absolute from administration of consumption of excessive fluid or it can be relative secondary to failure of the pumping mechanisms of the heart from various causes. In the former case, the pumping force of the heart cannot keep up with the additional fluids. In theory, excessive fluid administration or consumption could actually result in the heart's pumping mechanisms failing through over-distension of the ventricles. In the latter case (examples of which include myocardial infarction, cardiomyopathy), fluid backs up from the left and right ventricles of the heart leading to an increase in interstitial fluid buildup in various tissues. This includes the lungs, which may result in a state of pulmonary edema leading to lung injury, hypoxemia, and potential death requiring such interventions as tracheal intubation and mechanical ventilation.

Because central or intracardiac volume plays an important role in the diagnosis and management of many chronic and acute disease states, it is helpful to have some measure of it. Conventionally, the major measure of central vascular volume has been to measure pressure either within the right atrium (or superior or inferior vena cava) or in the pulmonary artery. The former measure has been termed "central venous pressure" (CVP) and is the pressure within or very near to the right atrium. The latter measure has been termed "pulmonary artery pressure" (PAP) and when a certain device is used to occlude the forward flow in a pulmonary artery, the "pulmonary artery occlusion pressure" (PAOP). PAOP is believed to reflect the pressure within the left atrium which is in turn believed to represent the pressure within the left ventricle. It is important to understand that pressure measurements in these cases are not volume measurements, Conventionally it has been considered that these pressure measurements reflect volume within their respective areas where the measurement is being made. CVP, PAP, and PAOP have been used to assess the volume status of patients and specifically the "preload" of the heart.

"Preload" is a concept relating to the Frank-Starling law in which the volume status of the patient is adjusted (usually increased) to produce an optimal increase in cardiac output that can be induced by fluid administration alone. This fluid administration distends the contracting fibers of the heart to a length which optimizes the contractile force. It is considered optimal to follow both cardiac output and volume status simultaneously as to create cardiac output-volume/pressure curves in which CVP, PAP, or PAOP is used as a surrogate of volume. Fluid is administered until no further increase in cardiac output is noted. The CVP, PAP, or PAOP is noted and additional volume is provided to keep one or more of these pressures the same. If intravenous inotropic agents or mechanical devices are used to increase cardiac output further, the CVP, PAP, and PAOP generally falls and additional fluid administration is then warranted. Conversely, too much intravascular volume can over-distend the heart pushing the heart muscle past its optimal length for maximum contraction, which will result in a decrease in cardiac output. In these situations it is helpful to reduce preload to the heart in order to restore optimal cardiac output. This reduction in preload can take place by one or more processes including diuresis, venodilation, or afterload reduction. In each situation it is helpful to understand the magnitude of the change by measuring either CVP, PAP, or PAOP while simultaneously measuring cardiac output and/or a measurement of end-organ perfusion. In summary, it is helpful to have a measure of central intravascular volume as measured by either CVP, PAP, or PAOP.

Recently, a specially modified pulmonary artery catheter has been developed which provides a measurement of volume status and preload called "right ventricular end-diastolic volume index" (RVEDVI). A Cariou, I Laurent, JF Dhainaut, "Pulmonary artery catheterization: Modified catheters. Principles and practice of intensive care monitoring" (1998). RVEDVI is not a pressure measurement but is based on flow through the right ventricle. This measure is said to be a good indicator of preload.

Knowledge of volume status and cardiac preload is beneficial in many disease states for both diagnosis and treatment purposes. Currently, there is no non-invasive method for doing so, and the major means to measure intravascular pressure-volume is by placement of catheters into the central circulation such as the pulmonary artery catheter and its derivatives or central venous catheters. It is no simple matter to insert these catheters. Complications known to be associated with their use include infection, arrhythmia, pneumothorax, hemothorax, chylothorax, laceration of the subclavian, carotid, and femoral artery, air embolism, and retained intravenous guidewires. Thus they are not suited as screening tools and it is difficult to use them for long-term management. There is also considerable expense involved in their use along with the need for other accessories such as a fluid column as part of the pressure transduction process.

Knowledge of volume status and cardiac preload being beneficial in many disease states for both diagnosis and treatment purposes, it would be valuable if such a measure could be made less invasively than with present methods, especially noninvasively.

U.S. Pat. No. 4,566,462 (issued Jan. 28, 1986 to Janssen), for "Venous Pressure Measuring Method and Apparatus" is limited to determining venous pressure, and does not disclose determining central venous pressure. Janssen noninvasively determines blood pressure using an inflatable cuff capable of exerting pressure on a selected vein.

U.S. Pat. No. 5,447,161 (issued Sep. 5, 1995 to Blazek et al.) for "Measurement Device for Non-invasive Determination of Blood Pressure in the Veins and Arteries", is concerned with determining blood pressure in the veins and arteries of fingers and toes. Particularly, Blazek et al. attach an air band (2) to a big toe and peripheral to the air band, apply a photoplethysmographic reflection (PPG) sensor (1) (both of which are connected to a blood pressure monitor (3)), record occlusion pressure $P_o$ in the finger band, the vein signal, and the artery signal, and raise air pressure $P_o$ in the band. When $P_o$ equals vein blood pressure $P_v$, the vein signal begins to rise because the blood in the veins flowing from the toe through the band is obstructed, such that the pressure in the vein can be determined. The arterial inflow into the measured area peripheral to the band is not yet impeded, so that the vein signal initially continues to rise, and the blood inflow is not impeded by the band barrier until the occlusion pressure reaches the $P_d$ value of the pulsating arterial pressure. Blood pressure values $P_v$, $P_d$ and $P_s$ are determined by the correlation of a direct current (d.c.) signal with $P_o(t)$. Blazek et al. do not teach intravascular volume measurement, but rather, are pertinent to pressure-related situations such as early detection of thrombosis and diagnosing vein pressure behavior. Blazek et al. does not teach detection of dehydration, congestive heart failure, renal failure, cardiogenic shock, traumatic shock, hemorrhagic shock, septic shock, etc. The Blazek et al. technology is not generally applicable for determination of central intravascular pressure and volumes because their method as taught measures pressure too distal to the central circulation which would in turn overestimate central vascular pressure and hence volume.

Too-distal measurements, such as those of Blazek et al, have not conventionally been usable in determining central intravascular pressure and volumes, because overestimation would result. The overestimation would have two sources: 1) pressure in veins distal to the axillary and brachial vein will be higher and 2) as a vein is occluded (prior to collapse) venous return will begin to be impeded.

Other factors in making pressure determinations in small veins (such as the determinations of Blazek et al.) unreliable is that the these small veins are relatively sensitive to temperature, catecholamines, vasoactive peptides, gravity, edema and other factors. Thus conventional methods (such as those described by Blazek et al) that rely upon small veins are not sensitive enough to determine true intravascular pressure of a vein as that pressure relates to the pressure within the central venous compartment (right atrium, superior vena cava, inferior vena cava). As represented by Blazek in FIG. 5 the normal venous pressure in the provided example for a normal state was 18.9 mmHg. This is likely to be 3–5 times higher than the brachial-axillary pressure and hence the central venous pressure. In fact, the normal pressure in small post-capillary veins is slightly less than than half the value reported by Blazek (approximately 7 mmHg: Guyton: Textbood of Medical Physiology, $6^{th}$ addition, W. B. Saunders Co: Philadelphia). This venous pressure drops further as the vein structure enlarges proximally (because veins get larger towards the central circulation and there is a pressure drop due to venous resistance from distal to more proximal venous structures).

U.S. Pat. No. 5,040,540 (issued Aug. 20, 1991 to Sackner), discloses measuring central venous pressure (CVP) based on changes in the dimensions of the neck. Sackner discloses a neck set-up and another stocking cap transducer set-up. The methods proposed by Sackner are not usable in patients over about 18 months due to the physiological basis for the CVP measurement no longer being present after cranial bones fuse in normal growth. Also, Sackner recognizes that neck volume changes detected by his transducers may be from breathing, not just from changes in blood volume, and he resorts to various methods for removing the breathing-related component, making Sackner's CVP measurements of dubious accuracy.

U.S. Pat. No. 5,904,143 (issued May 18, 1999 to Policastro et al.) discloses a non-invasive pointer-device for estimating CVP. The Policastro pointer device is not particularly accurate, and, as the inventors refer to the technology themselves, is more along the lines of an estimate.

In sum, newly available noninvasive methods (such as electrical impedance measures of intrathoracic blood volume, etc.) proposed by others cannot distinguish between intra and extravascular fluid and thus are not useable when accurate CVP measurement is needed. As a result, currently the measurement of CVP unfortunately has been limited to invasive measurements, with the current "gold standard" for measurement of central venous volume being the Swan-Ganz or pulmonary artery catheter (PAC), introduced in 1970 or the CVP catheter. While the PAC or CVP catheter can accurately measure central intravascular pressure (right atrial and right ventricular pressures, pulmonary artery pressures, and pulmonary artery occlusion or "wedge" pressure), use of this catheter constitutes an invasive technique associated with numerous complications (infections, clots, arrhthmias, etc.).

Thus, technology for monitoring CVP non-invasively while obtaining results as accurate as for invasive measurements would be a medical advance. Health benefits to patients would be seen by removing the disadvantages of invasive CVP measurement while maintaining the accuracy of such invasive measurements.

SUMMARY OF THE INVENTION

The present invention non-invasively determines CVP and provides information concerning relative changes in intravascular volume. To do so, certain curves are plotted based on non-invasively determined patient information obtained by applying a controllable variable (such as degree of incremental inflation/deflation of a non-distally-applied vascular cuff (such as voltage applied)), taking certain measurements (such as pressure measurements) from the patient, plotting a curve based on the datapoints (such as a volume increase curve or a volume decline curve). Pertinent, accurate CVP and/or blood volume information is obtained from at least one feature (especially such as slope) of the non-invasive-based curve. Thus, the invention advantageously provides accurate CVP information without the risks and disadvantages of invasive measurement.

An important purpose of the present invention is to noninvasively measure CVP and indicators of intravascular central volume and preload, such as for diagnostic and treatment.

In order to accomplish these and other objects of the invention, in a first preferred embodiment, the invention provides an intravascular pressure and volume-based non-invasive diagnostic method, comprising: (a) from a patient, taking non-invasive intravascular pressure and volume measurements; (b) plotting the non-invasive intravascular measurements as pressure and volume change curves; and (c) determining (i) an overall slope of the volume change curve, (ii) a maximum slope of the volume change curve and/or (iii) when the volume change curve is a volume decline curve, a threshold of the volume decline curve.

The invention in a second preferred embodiment provides a method of non-invasively determining CVP from an identified pressure measurement during a cuff inflation and/or deflation procedure from which is subtracted a baseline cuff, to determine CVP. comprising at least the step of determining $CVP \sim P_{max\ slope} - P_0$. $P_0$ is a measured initial pre-inflation pressure in an inflatable vascular cuff applied at a non-distal part of the patient. $P_{max\ slope}$ is a measured pressure at a maximally sloping part of a curve consisting of data points (x,y), with x being a volume variable (an exemplary example being variable x controlled by using voltage used in inflating the vascular cuff) and y being time.

In a third preferred embodiment, the invention provides a system for non-invasively measuring intravascular central pressure and/or volume, comprising: (a) a non-invasive inflatable cuff supplying data to a data processing system; (b) a non-invasive cuff inflator receiving control instructions form and/or sending data to the data processing system and (c) a non-invasive volume sensitive detector sending data to the data processing system. In a further preferred embodiment, the inflatable cuff is sized for surrounding an extremity in an upper region.

Some further aspects and features of the invention are now mentioned, without the invention being limited thereto.

With regard to a volume change curve according to the invention, further embodiments of the invention provide that the overall slope of the volume change curve may be related to right ventricular compliance and venous return; that changes in the overall slope of the volume change curve are related to ventricular compliance and venous return, etc.

In the inventive methods, devices, and systems, the CVP determination may be based on the cuff pressure at the volume change curve maximum slope or on the volume decline curve threshold. Further, such methods, devices and systems may include one or more of the following: absolutely determining CVP; inflating and/or deflating a vascular cuff surrounding an extremity upper part; determining the rate of venous volume change upon deflation of a vascular cuff surrounding an extremity upper part; determining the rate of venous volume change upon inflation of the vascular cuff; determining the threshold of venous volume change upon deflation of a vascular cuff surrounding an extremity upper part; measuring pressure for a large vein; surrounding an upper extremity with an inflatable cuff, and inflating the cuff while taking pressure and volume measurements; data-processing by a computer comprising an analogue-digital converter and a data acquisition system; pressure monitoring by providing a sensor between the cuff and skin overlying the vessel being monitored; and/or placing an occluding cuff on an ankle and/or a jurist, etc.

A particularly preferred embodiment of the invention provides for non-invasively detecting volume sensitive data for a distal part of the extremity by operating a volume sensitive detector selected from the group consisting of a mercury-in-silastic strain gauge, a bioimpedance device, a photo device, a plethysmography device, a laser Doppler device and a spectroscopic volume detection device.

The invention also provides methods, devices and systems wherein one or more of the following features are provided: an inflatable cuff is electrically and pneumatically connected to a programmed cuff inflator device; a computer processor receives pressure measurements from a cuff; the volume sensitive detector sends information to a computer via a signal amplifier; etc.

The inventive methods, devices and systems in further embodiments may include one or more of the following: determining whether intraabdominal pressure is elevated by determining pressure in large leg veins; titration of fluid resuscitation, positive end-expiratory pressure (PEEP), and/or titrating fluid therapy; applying non-invasively determined central venous pressure along with non-invasive measures of cardiac output (such as carbon dioxide rebreathing, Doppler, bioimpedance, arterial waveform analysis, etc.); fluid therapy titration based on a magnitude of non-invasively determined volume changes during deep inspiration; applying non-invasive measures of extravascular lung water to differentiate lung injury from fluid excess and/or titrate fluid therapy; applying non-invasive measures of extravascular water to differentiate total body fluid excess and/or titrate fluid therapy; applying a non-invasive measure of extravascular lung water or of extravascular water (such as impedance cardiography (ICH) data or bioimpedance vector analysis (BIVA) data), etc.

For providing higher sensitivity, the inventive methods, systems and devices may include a first non-invasive cuff and at least one additional occluding cuff, the additional occluding cuff sized to an ankle and/or a wrist.

DETAILED DESCRIPTION OF PREFERRED EMBODIMENTS OF THE INVENTION

Figure 1:
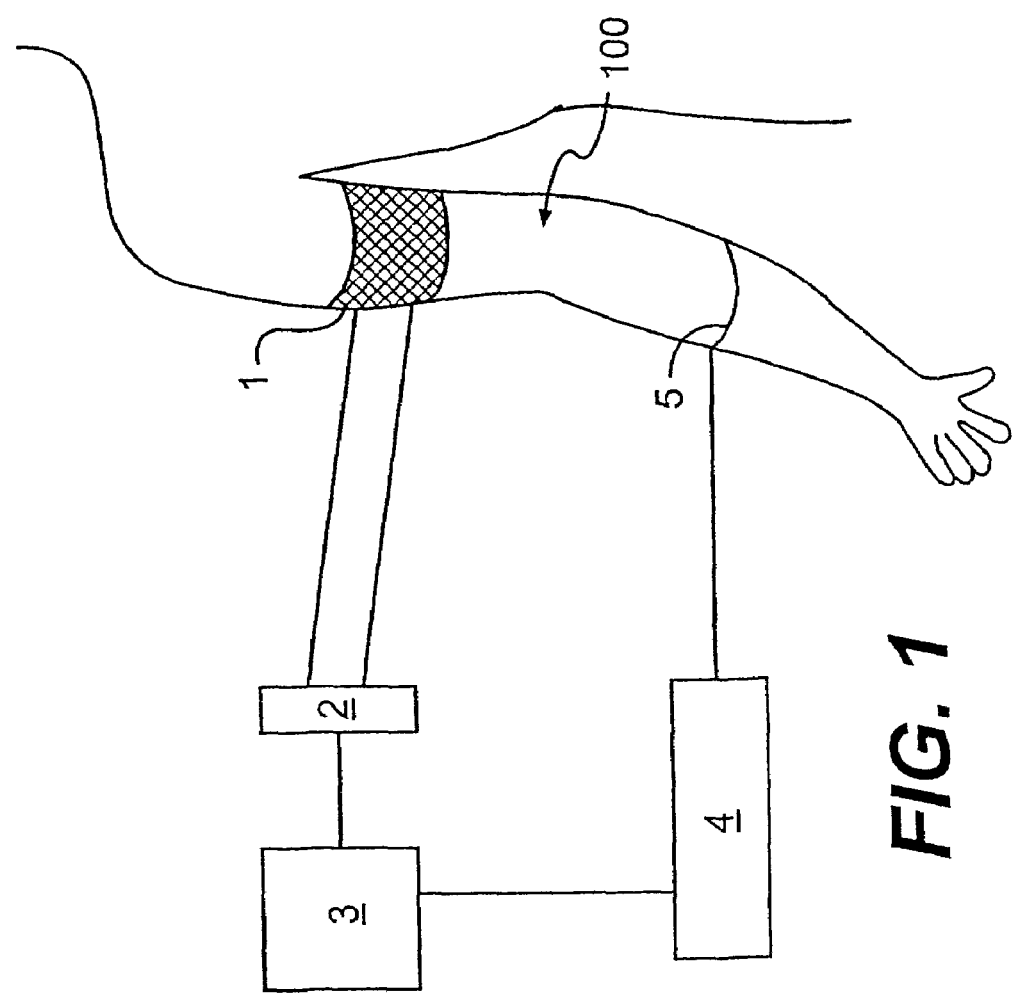
FIG. 1 is a diagrammatic representation of a system according to the invention for noninvasive measurement of CVP, and/or monitoring and/or optimizing central vascular volume and preload.

In a preferred embodiment, shown in FIG. 1, the invention provides a system for non-invasively measuring intravascular central pressure and/or relative volume changes, comprising: (a) a non-invasive inflatable cuff 1 applied to the patient's upper arm 100 supplying data to a data processing system 3; (b) a non-invasive cuff inflator 2 receiving control instructions from and/or sending data to the data processing system 3; and (c) a non-invasive volume sensitive detector 4, connected to, for example, a strain gauge 5 attached to the patient's forearm, sending data to the data processing system. Advantageously, the invention preferably may use devices already commercially available and in use in other medical work, such as a combination of cuff and inflator devices conventionally used for arterial blood pressure measurement and a device conventionally used to perform venous plethysmography for forearm arterial blood flow. Such devices are newly used in the present invention for non-invasively measuring intravascular central pressure and/or volume.

As the non-invasive inflatable cuff supplying data to a data processing system may be used any mechanically, controllably inflatable and deflatable cuff, e.g., devices conventionally used to measure arterial blood pressure, such as Hokanson SC10 or SC12. The cuff may contain an area for directing pressure over a vein of interest (such as an axillary vein, a brachial vein or a femoral vein), and/or may include a pressure transducer that measures force between the cuff and skin overlying the vein of interest. Also, there may be used any other cuff or device that occludes venous outflow from a vein of interest (such as an axillary vein).

As the non-invasive cuff inflator receiving control instructions from and/or sending data to the data processing system may be mentioned cuff inflators conventionally used to measure arterial blood pressure, such as Hokanson TD312.

As the non-invasive volume sensitive detector sending data to the data processing system may be used any distal sensor capable of measuring small volume (i.e., on the order of 0.5 to 1%) changes in the extremity or its parts distal to the point of occlusion, e.g., devices conventionally used to perform venous plethysmography for forearm arterial blood flow, such as a Hokanson EC-4 plethysmography device. Signal amplifiers (such as Biopac DA100C) and/or interfaces (such as Biopac UM100C) may be used with the volume sensitive detector.

Although curve-plotting according to the invention may be performed in a non-computerized embodiment, most preferably in practicing the invention a data processing system is used. The data processing system may be any system that controls and/or receives and processes information from the cuff and receives and/processes information from the volume sensitive detector, e.g., a computer with analogue to digital converting capabilities and software for controlling cuff inflation and deflation while simultaneously assessing volume changes. As a preferred example may be mentioned a multi channel physiologic recording instrument such as an AR-6 SIMUTRACE.

In an exemplary system of noninvasive measurement of CVP according to the invention, pressure (vascular cuff and/or pressure sensor between the skin and cuff is non-invasively monitored at a non-distal point on the patient such as at an upper extremity (such as on the upper arm such as along the axillary or brachial vein or on the upper thigh such as along the femoral vein). Examples of such non-invasive monitoring are to apply an inflatable cuff and to measure pressure inside the cuff with a transducer; to attach or incorporate a pressure transducer onto the surface of the cuff that is in contact with that area of the skin overlying the brachial, axillary, or femoral vein, etc. When a transducer is used to measure pressure within the cuff, preferably this value is constantly reported to a computer during inflation and deflation.

When an inflatable vascular cuff is used, the inventive method provides for inflating the vascular cuff above the central venous pressure but below arterial diastolic pressure. For almost all practical purposes a vascular cuff pressure of 30–40 mm Hg can be used since central venous pressures of this magnitude are usually inconsistent with life and diastolic arterial pressure is usually higher than this range.

A preferred example of cuff inflation is to inflate the cuff rapidly to a pressure of 40 mm Hg. At 40 mm Hg, venous outflow from the arm or leg is halted because this pressure is above the CVP and hence the axillary, brachial, or femoral vein pressure. Because 40 mm Hg is still normally below arterial diastolic pressure while above venous pressure, blood flow into the distal extremity (arm or leg) continues, resulting in an increase of volume into the limb distal to the point of venous occlusion.

The length of venous occlusion from the vascular cuff can be maintained for various lengths of time but is usually maintained until no further significant changes in volume are noted. An example of no further significant changes in volume is a plateau of the volume signal such that the volume signal changes less than 5% over 30 seconds.

When no further significant changes in volume are observed, the vascular cuff is deflated. Once the pressure occluding the axillary, brachial or femoral vein is reduced below its closing pressure, the volume in the limb distal to the point of occlusion begins to rapidly decrease signaling restoration of venous flow. Analysis of the slope of this volume drop reveals that the derivative of the curve (e.g., the slope) represents venous flow and hence the cuff pressure at the maximal slope represents mean pressure within the brachial, axillary or femoral vein, which represents CVP. The pressure as measured within the vascular cuff 1 or by a pressure transducer between the cuff 1 and skin overlying the axillary, brachial, or femoral vein at this point thus represents CVP. See, e.g., FIG. 2.

Figure 2:
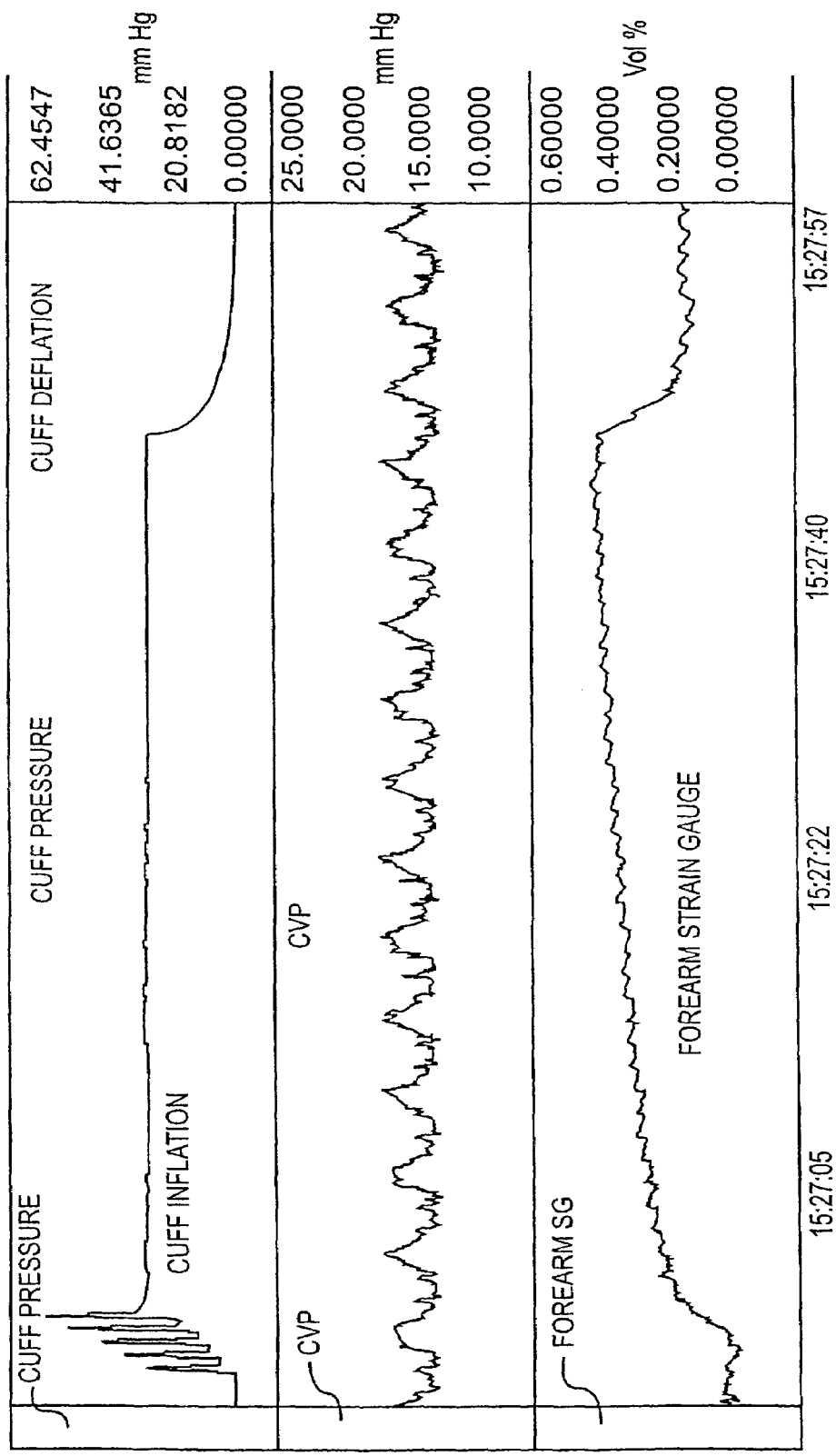
FIG. 2 is a graphical demonstration of simultaneous cuff pressure, invasively measured CVP and forearm mercury-in-Silastic strain gauge volume % recording.

As shown in FIG. 2, as vascular cuff pressure is increased, the volume in the distal arm increases, as noted by the strain gauge 5. When the vascular cuff pressure is decreased, the volume in the forearm is decreased as noted by the strain gauge 5.

Alternatively, the vascular cuff 1 may be slowly inflated. The point of maximum rise in slop (volume over time) distal to the cuff represents the occluding pressure within the vein, which in turn represents the CVP.

The measurements may be made more sensitive by inflation of an additional vascular cuff around the wrist or ankle above arterial systolic pressure to reduce the time lag of volume increase in the foreman or calf that may occur from venous filling of the hand or foot respectively. The inflation of the wrist or ankle vascular cuff can be done in several seconds and does not add significant additional time to the measure of venous pressure.

The rate of inflation and deflation can be varied such as inflation and deflation at a rate of 1 mm Hg/sec. The preferred method is rapid inflation while holding the inflation for 30–60 seconds followed by rapid deflation. This routine is demonstrated in FIGS. 2 and 3 in a subject who was undergoing invasive CVP monitoring as a part of prescribed care.

Figure 8A:
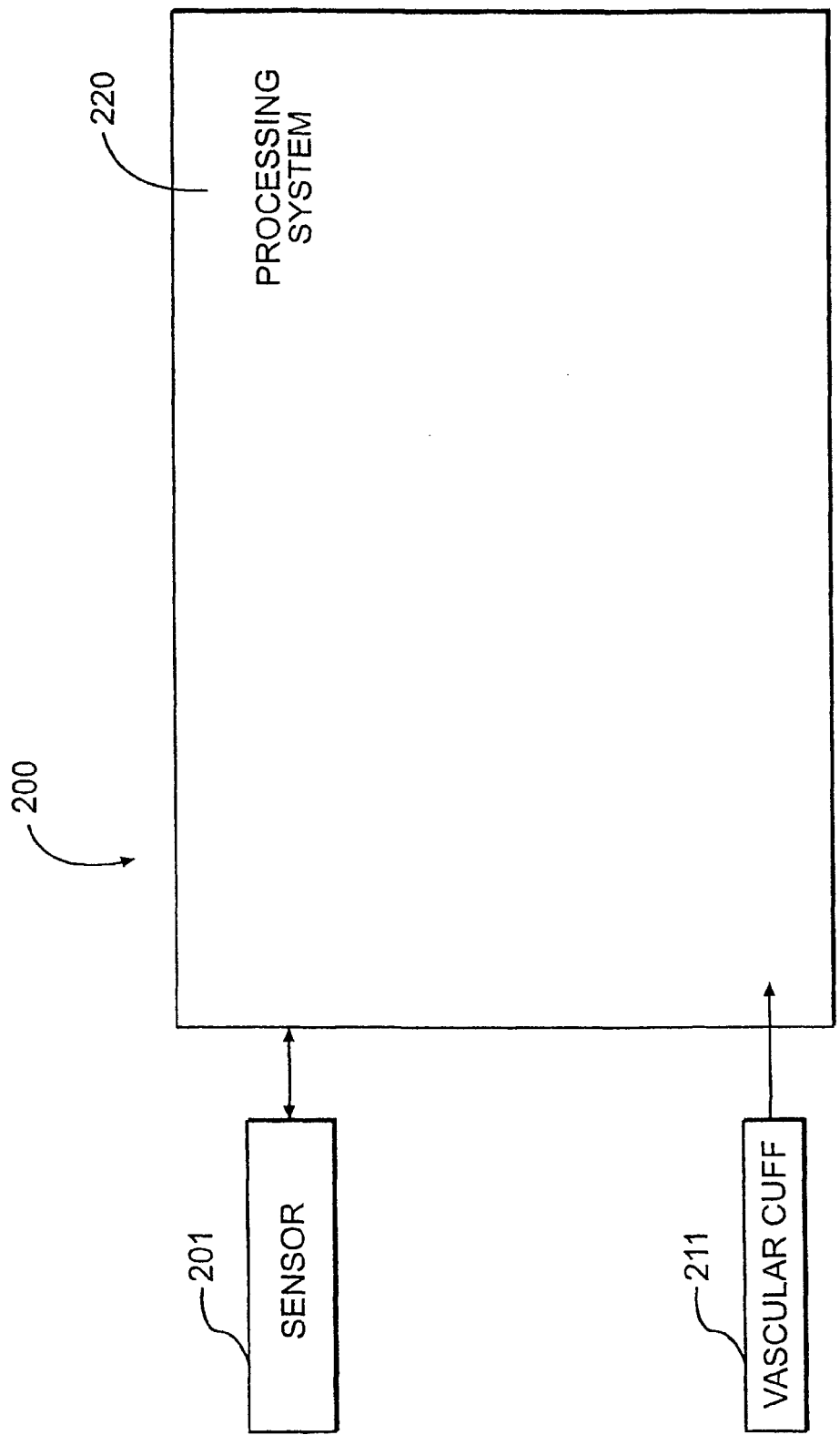
FIGS. 8A–8C are block diagrams of exemplary non-invasive CVP monitoring systems according to the invention.

Referring to FIG. 8A, a non-invasive CVP monitoring system 200 according to the invention may comprise a sensor for measuring volume change 201 (such as a mercury-in silastic or other sensitive device for measuring volume change) receiving data from and sending data to a processing system 220, the processing system 220 receiving data from a vascular cuff 211. As examples of the vascular cuff 211 are inflatable vascular cuffs which can be placed at a non-distal part of a patient, such as on the upper arm or leg. The processing system 220 of FIG. 8A is discussed below with regard to FIGS. 8B and 8C in which exemplary processing systems according to the invention are shown.

Figure 8B:
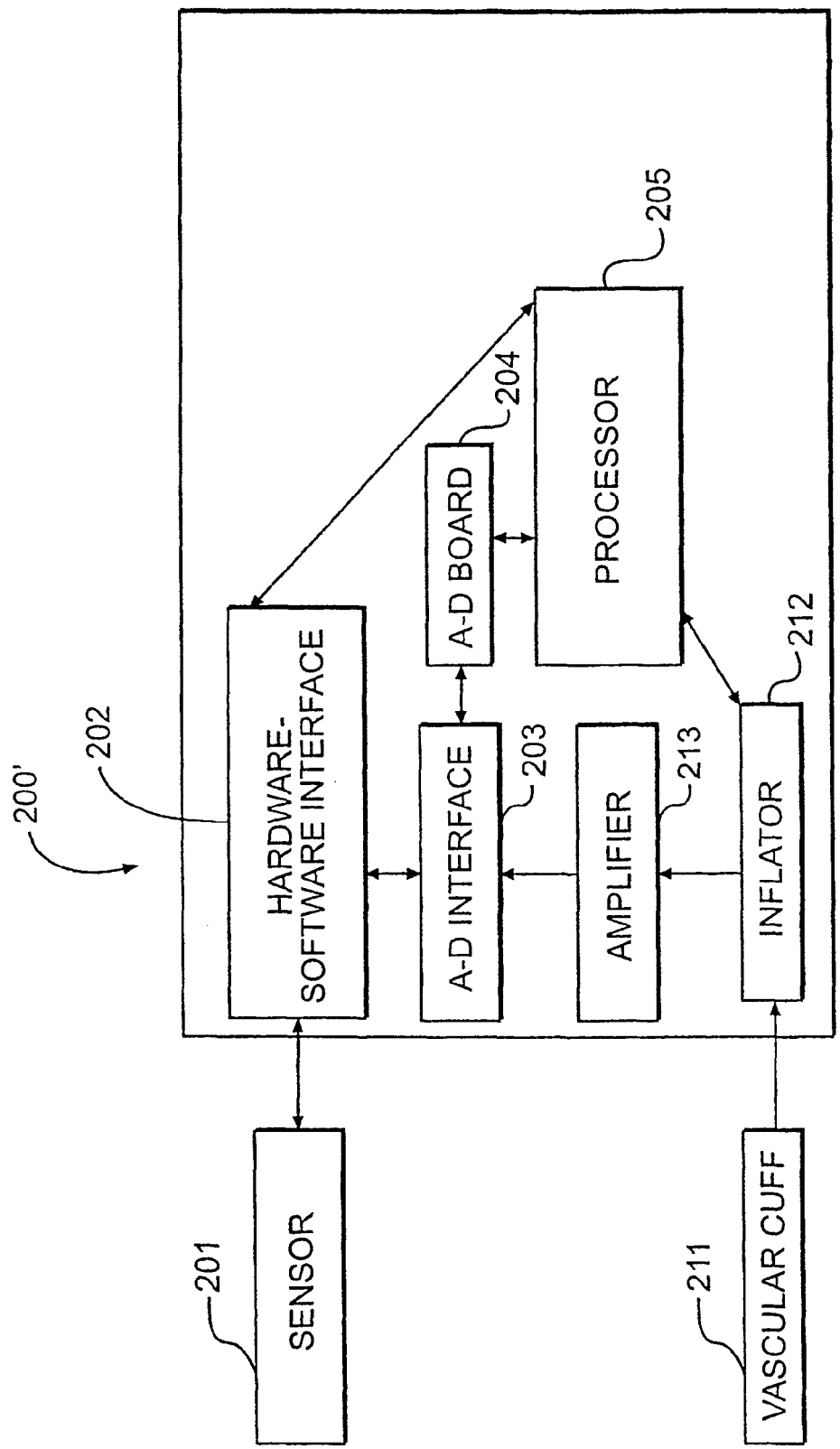

As shown in FIG. 8B, in a preferred embodiment of a non-invasive CVP monitoring system 200' according to the invention, a sensor for measuring volume change 201 (such as a mercury-in silastic or other sensitive device for measuring volume change) is connected to a hardware-software interface 202 (such as a plethysmograph or other hardware-software interface depending on the type of sensor). As interface 202 may be used any interface which can be zero balanced to detect and quantitate volume increases or decreases for the lower extremity (such as forearm, or other limb or digit) to which the sensor 201 is applied. Particularly preferred as interface 202 is a plethysmograph, especially a signal-amplifying plethysmograph. The signal received by the interface 202 is sent (via A-D analogue-to-digital) interface 203) to an A-D board 204 which digitizes the data and then sends the data to a processor 205 (such as a microprocessor unit (computer)), where the data may be stored and/or displayed (such as display 206 on FIG. 8C). The vascular cuff 211, which can be placed on the upper arm or leg, is inflated and deflated via an inflator 212, preferably an inflator with a pressure transducer (such as the inflator with a pressure transducer 212A in FIG. SC), most preferably an automated inflator operating at a controlled rate determined by the processor 205. This inflator 212 preferably also monitors the pressure in the vascular cuff 211 as measured via a pressure transducer, with the output from this transducer first amplified (at the amplifier 213) and then sent (via the A-D interface 203) to the A-D board, after which the output may be sent to the vascular cuff 211. The processor 205 (such as a microprocessor and associated software) examines the rate of volume decline (venous outflow) following the onset of cuff 211 deflation and finds the maximum slope. The pressure in the vascular cuff 211 at this point is measured. The baseline cuff 211 pressure (before inflation) is subtracted, and this difference is used as an estimate of central venous pressure. That is, as an equation, an inventive system may non-invasively determine CVP as follows:

$$CVP \sim P_{max\ slope} - P_0,$$

where $P_0$ is a measured initial pressure in the vascular cuff 211 before inflation and $P_{max\ slope}$ is a measured pressure at a maximally sloping point of a curve consisting of data points (x,y), with x being the volume variable and y being time. Preferably variable x may be controlled by using voltage used in inflating the cuff.

Figure 8C:
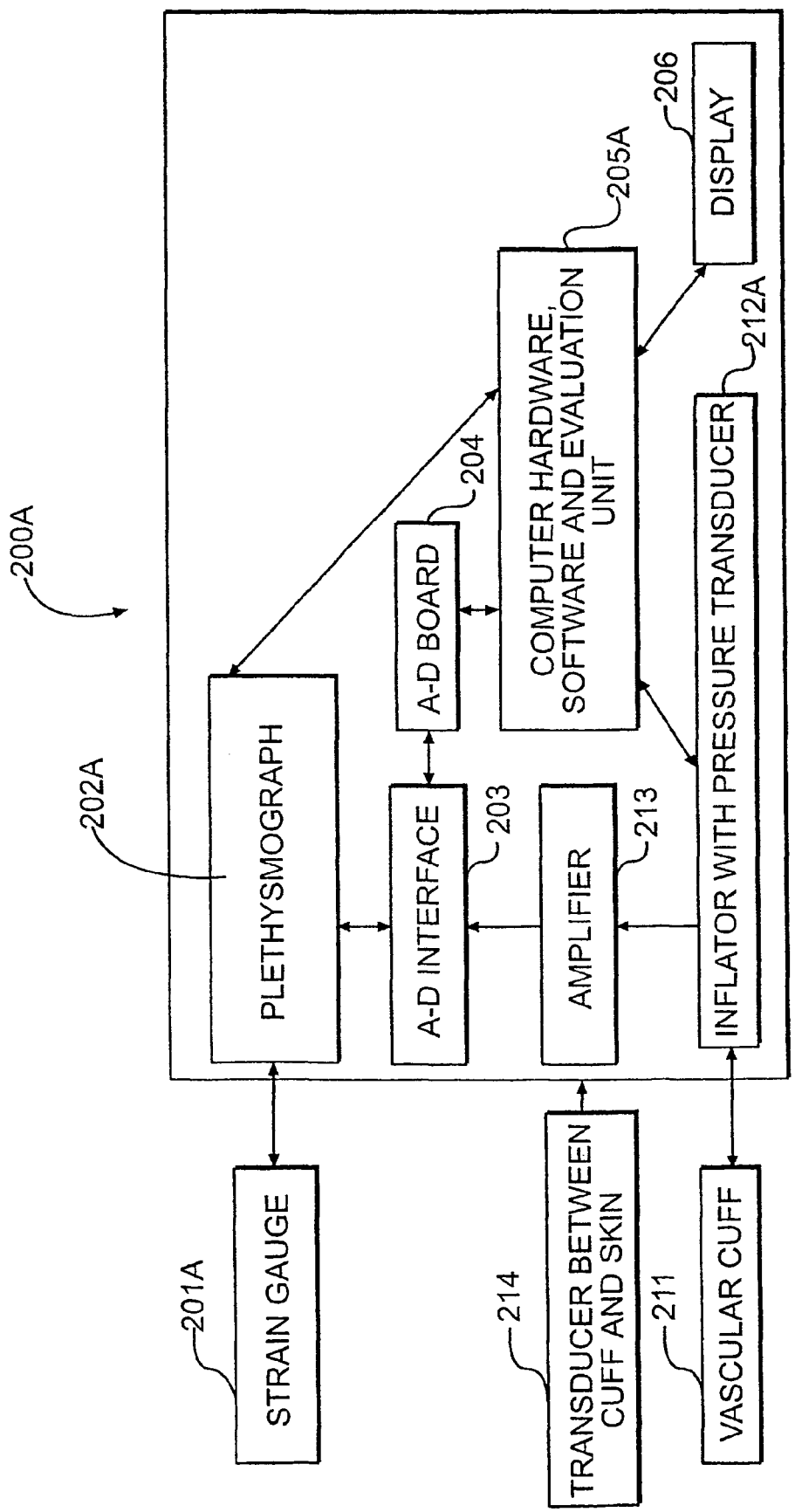

Most preferably, all measurements, control and display are handled via a central microprocessor unit and associated software. As shown in FIG. 8C, a display 206 may be used to report values and offer menu guidance.

Alternatively, instead of using vascular cuff pressure, a sensor may be placed between the cuff and the tissues of the arm or leg to measure the pressure that the vascular cuff exerts on the tissue overlying the axillary, brachial, or femoral vein. This transduced pressure is amplified and sent to the A-D interface followed by the A-D board and then the computer.

A distal measurement (such as volume measurement, impedance measurement, flowmetry, spectroscopy, etc.) is carried out on an area distal to the upper extremity pressure measurement (such as, when an upper arm area is being measured, a distal area thereof including hands, fingers; when an upper leg area is being measured, a distal area thereof including feet, toes), or combinations of distal areas. For taking distal measurements as examples may be mentioned mercury-in-Silastic strain gauges, photo or other plethysmography, bioimpedance measurement sensors, laser flowmetry, near-infrared sensors, spectroscopy, other sensors detecting small (such as about 0.5 to 1%) changes in volume in the limb distal to the point of cuff occlusion, etc. Preferably the set-up positions a vascular-cuffed, distally-sensored arm or leg level with the right atrium.

Preferably a distal measurement-taking sensor (such as a volume or impedance based sensor, etc.) is connected to a computer system. Most preferably, an inflatable cuff is used for upper extremity measurement and a computer system receives measurement data of distal volume changes and upper extremity pressure data. Especially preferred is a computer system that relates distal volume changes to upper extremity pressure data, such as comparing distal volume changes in response to inflation and deflation of a vascular cuff applied to an upper extremity. As the computer system may be mentioned a computer-data acquisition system with analogue-to-digital converter capabilities and control mechanisms to allow for timed and controlled inflation and deflation of the proximal arm or leg vascular cuff with simultaneous detection and analysis of volume changes in the limb distal to the inflated vascular cuff during inflation and deflation of the cuff.

Figure 5:
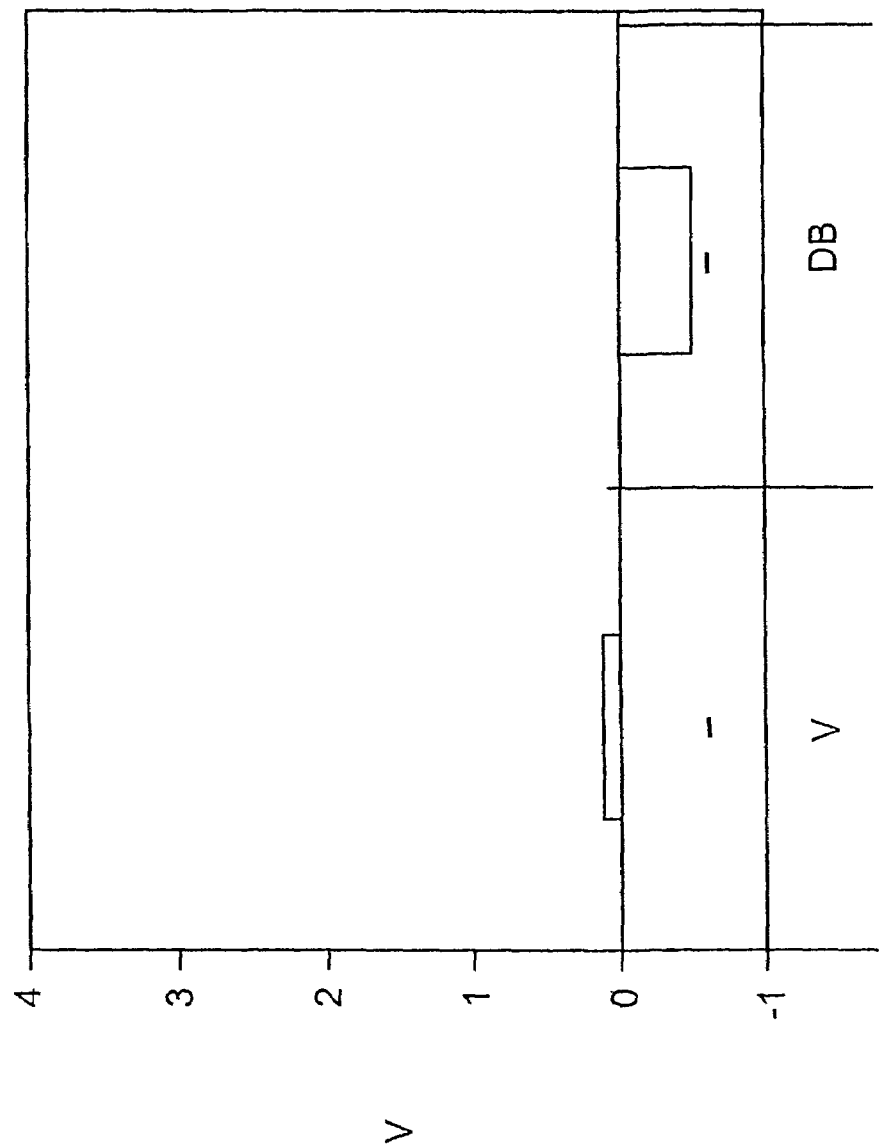
FIG. 5 is a graph of strain-gauge measurement of forearm intravascular volume represented by change in voltage during baseline (V) and during deep inspiration (DB).
Figure 6:
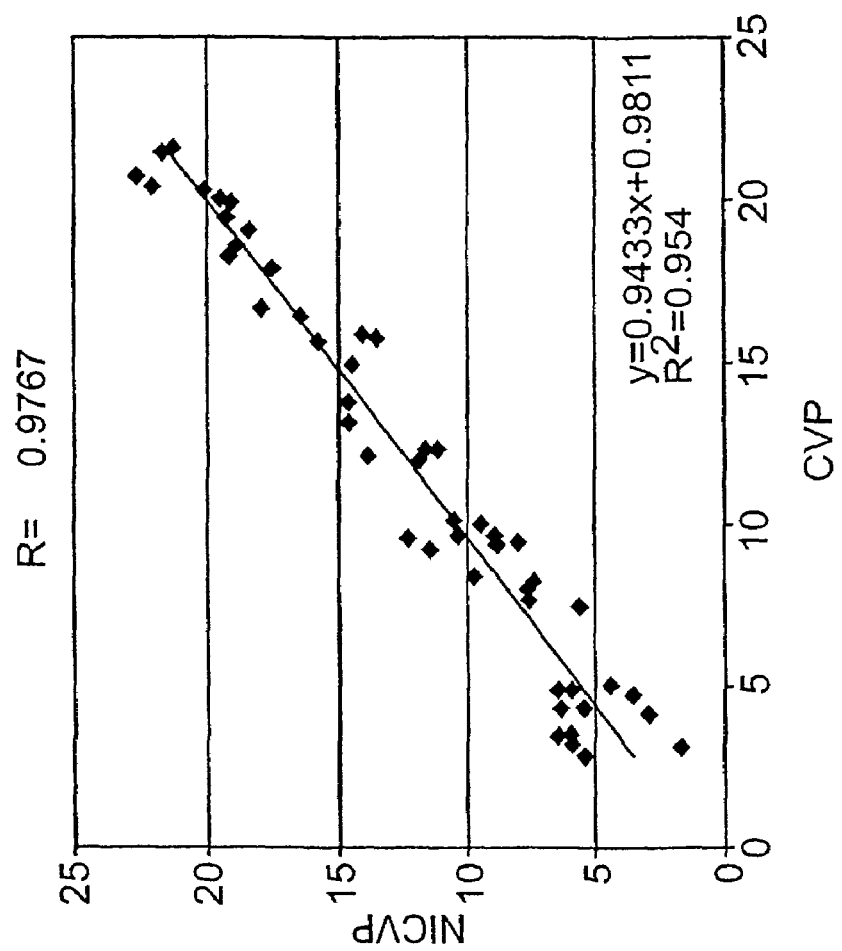
FIG. 6 is a graph of NICVP versus invasive CVP, based on actual clinical data points from forearms of human patients.

Intravascular volume may be determined from a strain-gauge measurement of the lower part of the extremity, with the lower extremity (such as forearm) intravascular volume represented by change in voltage during baseline (V) and during deep inspiration (DB). An example of such measurements is shown in FIG. 5. A volume decrease may be detected through increase in venous return by deep inspiration.

An exemplary device for noninvasive measurement of CVP according to the invention may be seen with reference to FIG. 1. An inflatable vascular cuff 1 is non-invasively applied to surround a patient's extremity at an upper part. The inflatable vascular cuff 1 preferably is formed to ensure pressure to be focused on a particular vascular structure(s) (such as a relatively large vein) as the cuff is inflated and pressure is circumferentially produced. The inflatable external device 1 is shown applied to an upper arm 100, but as mentioned above, may also be applied to a thigh. Inflatable vascular cuffs for pressure measurement are known to those skilled in the art, see, e.g., U.S. Pat. No. 4,566,462 (Janssen). The inflatable cuff 1 optionally includes an embedded pressure sensor, such as a Milar brand button pressure transducer. The cuff 1 may be manually inflatable or controllably inflated by a computer, preferably inflatable by a computer. A transducer may measure pressure within the cuff 1 with the measured pressure reported (preferably constantly reported) to the computer during inflation and deflation. Alternatively, a pressure transducer may be attached or incorporated onto the surface of the cuff 1 that is in contact with that area of the skin overlying the brachial, axillary, or femoral vein, with pressure as measured by this transducer is reported (preferably continuously) to the computer.

In the preferred embodiment shown in FIG. 1, the cuff 1 is electrically connected to a programmed cuff inflator 2 that reports pressures to a processing system 3 (such as a computer with analogue-digital converter and a data acquisition system). The computer 3 provides information to a signal amplifier 4 which is connected to a volume sensitive detector 5 (such as a mercury-in-silastic strain gauge, a bioimpedance device, photo or other plethysmography device, laser Doppler, spectroscopic volume detection device, etc.).

The functioning of the system of FIG. 1 may be understood in view of the following.

First, the pressure within peripheral veins such as the axillary, brachial, and antecubital vein are almost equivalent to those measured in the right atrium as CVP. S E Ricksten, A Medegard, I Curelaru, B Gustavsson, L E Linder, "Estimation of central venous pressure by measurement of proximal axillary venous pressure using a 'half-way' catheter," Acta Anaesthesiol Scand, 30(1):13–7 (1986); D Amar, J A Melendez, H Zhang, C Dobres, D H Leung, R E Padilla, "Correlation of peripheral venous pressure and central venous pressure in surgical patients," J Cardiothorac Vasc Anesth, 15(1):40–3 (2001).

Second, the relationship between intravenous pressure within the antecubital and thus brachial and axillary vein are equivalent to the pressure within a blood pressure cuff applied over the brachial or axillary vein when the cuff pressure is increased above resting intravenous pressure. This relationship is linear over the range of clinically encountered central venous pressures. J R Halliwill, C T Minson, M J Joyner, "Measurement of limb venous complkiance in humans: technical considerations and physiological findings," J Appl Physiol, 87(4):1555–63 (1999).

Third, the rate of venous return from the arm is likely to be affected by several factors including cardiac output and central venous pressures.

Fourth, the above-mentioned relationships and observations are likely to be applicable to the lower extremities because pressure within the femoral and iliac veins have been demonstrated to be equivalent to central venous pressures as measured in the right atrium. K M Ho, G M Joynt, P Tan, "A comparison of central venous pressure and common iliac venous pressure in critically ill mechanically ventilated patients," Crit Care Med, 26(3):461–4 (1998); R Sheridan, A Nackel, M Lydon, L Petras, G Basha, "Infra-diaphragmatic central venous pressures reflect supradiaphragmatic pressures in stable burn patients," J Trauma, 47(2):300–2 (1999).

It is the rate of change of the volume sensing Method that is likely to indicate the occlusion or opening pressure of the vein, which is surrounded by the pressure build-up band (in our case vascular cuff). The present invention both makes absolute determinations of central venous pressure as well as observes changes in rate of venous runoff when the vascular cuff is deflated.

At a certain cuff pressure, the axillary vein will collapse. As long as cuff pressure remains well below the arterial diastolic pressure (normally about 80 mm Hg) for short periods of time (less than or equal to 30 seconds), arterial inflow will continue, and the volume of the arm distal to the cuff (including the forearm) will increase. The change in forearm circumference (and hence volume) at a pressure is measured (such as with a mercury-in-Silastic strain gauge, a water displacement plethysmograph, photoplethysmography, etc.). When forearm volume increases at the maximum rate, the cuff pressure will be noted as a reasonable estimate of CVP. In certain individuals with conditions which could compromise the measurements (e.g., obesity, edema, etc.), there may be used the rate of volume decrease in the forearm following rapid cuff deflation from a a pressure of 20–40 mm Hg. To further enhance accuracy, a miniaturized pressure transducer may be placed between the inner surface of the vascular cuff and skin or in the subcutaneous tissue or muscle for a closer measure of true vascular collapse pressure.

Although an exemplary form of the invention has been discussed with respect to application of the cuff 1 to the arm 100 in FIG. 1, it will be appreciated that other applications of a cuff are provided by the invention, such as to the thigh, calf, neck, etc. Such non-arm applications may be particularly important in the case of arm trauma.

The invention has many uses, especially in medical measurements, diagnosis, treatment, etc. For example, devices and methods according to the invention may be used on patients whose volume status is unclear, such as patients with suspected compensated or uncompensated shock state (traumatic, cardiogenic, septic), congestive heart failure, renal failure, etc. Because the invention provides devices that are free of the risks of invasive devices, the inventive devices may be used as an initial tool in assessing volume status of a patient. This assessment may occur in the prehospital setting, hospital ward, operating room, intensive care unit, emergency department, special care unit, cardiologists' offices, other places where progression/treatment of heart failure is measured, dialysis clinics, nursing homes, residences, etc.

Devices according to the invention preferably are used as part of a multiparametric monitoring system that noninvasively monitors multiple physiological parameters in shock and critically ill patients. Such a system provides more information than conventionally-used PACs and can be applied significantly earlier in a patient encounter. This feature in turn increases the potential to obtain information that would allow diagnostic and therapeutic decisions early enough in patient care to improve outcome.

The invention provides a new use for equipment commonly used to measure forearm blood flow (by measuring the rate of forearm volume increase), venous outflow obstruction (forearm volume decrease following handgrip exercise) and venous compliance (forearm volume changes following step changes in cuff pressure).

The inventive methods herein permit examination of the slope of venous return from an extremity during cuff deflation. When this measure is repeated in the same individual after repetitive fluid administration, there may be detected a decrease in the point at which the maximum slope had been previously occurring. The time at which the slope changes is identified as signaling the maximum amount of fluid the right heart is able to receive while still maintaining a maximum cardiac output. It may thus be interpreted that the CVP at which this occurs is the point of optimal preload. This strategy also may be used to indicate at which point fluid removal, afterload manipulation, or inotropic manipulation of the heart is optimal.

The system as diagrammed in FIG. 1 can be incorporated into other monitoring systems such as those which noninvasively measure cardiac output without the need for pulmonary artery catheterization. Such a system advantageously allows for production of Frank-Starling pressure-cardiac output curves in which volume was provided or reduced to produce maximum cardiac output while noting the level of CVP at which this maximum cardiac output is obtained. Additional fluid administration or fluid reduction is provided to maintain this CVP. In addition, other subsequent maneuvers to improve cardiac output such as use of inotropic agents, or manipulation of arterial blood pressure may reduce CVP. Thus the system could indicate that additional fluid administration should be provided to return CVP to the level previously shown to produce maximum fluid increases in cardiac output.

Repetitive examination may be performed of the slopes of venous run-off from the limb during vascular cuff deflation in response to fluid administration or fluid reduction as an internal response to optimize preload. When a human is challenged with additional intravascular volume that increases the right ventricular or central venous pressure, an increase in cardiac output results. This increase in cardiac output prevents accumulation of fluid in the venous bed of the tissues by essentially maintaining the rate of venous return. This also means that movement of fluid from the right heart matches movement of fluid from the left heart. The point at which fluid administration is not matched by changes in cardiac output means that fluid will begin to accumulate in the venous system of tissue beds. This in turn will be reflected by decreases in venous return to the right side of the heart since venous pressures are elevated out of proportion to cardiac output.

Also, this strategy has value to right ventricular end-diastolic volume index (RVEDI) monitoring in determining ventricular compliance and optimal preload. See L N Diebel, R F Wilson, M G Taggett, R A Kline, "End-diastolic volume. A better indicator of preload in the critically ill" [see comments], Arch Surg, 127(7):817–21, discussion 21–2 (1992); E H Kincaid, J W Meredith, M C Chang, "Determining optimal cardiac preload during resuscitation using measurements of ventricular compliance," J Trauma, 50(4): 665–9 (2001).

This approach also may be used when managing patients who require mechanical ventilation and the use of positive end-expiratory pressure (PEEP). PEEP is known to reduce venous return by increasing intrathoracic pressure because this increase in intrathoracic pressure is transmitted to the right heart and superior and inferior vena cava. Thus a level of PEEP which begins to interfere with venous return from an extremity as recognized by a changing slope when determining the CVP may alert the clinician that the PEEP should not be increased any further or that a change in cardiac output by either administration of fluid or the use of inoptric agents is required to overcome the adverse effects of PEEP on venous return.

Some volume sensitive measures (such as a mercury in-Silastic strain gauge) are sensitive enough to detect respiratory variation in the extremity volume during spontaneous inspiration. Deep inspiration increases the rate and volume of venous return to the right atrium and ventricle by reducing intrathoracic pressure. A mercury in-Silastic strain gauge, for example, may be used to detect a decrease in limb volume associated with deep inspiration (see FIG. 5). Intravenous administration until no further decrease in volume during inspiration may be indicative of optimal preload. The noninvasively measured CVP at that point would be kept by providing additional fluid (such as by intravenous provision of fluid, etc.). Conversely, the subsequent use of inotropes or afterload manipulation which changes preload resulting in reappearance of inspiratory pressure-induced changes in limb volume signals the need to administer additional volume (such as by the intravenous route) to maintain optimal preload.

Non-invasive CVP determination also may be useful to determine the presence of raised intra-abdominal pressure when measurements are taken from both the leg and arm. Abdominal compartment syndrome is a well-known complication of trauma which can cause splanchnic ischemia. The pressure within the abdomen is expected to be transmitted to the inferior vena cava which in turn is detected by measurement of pressure and venous return in the femoral vein using the non-invasive techniques of the invention. The measure may be made even more sensitive to the presence of increased intra-abdominal pressure by simultaneous comparison to a non-invasive measure of CVP made in the upper extremity.

Another novel use of noninvasive CVP measurement techniques is with noninvasive bioimpedance based measurement of extravascular lung water using impedance cardiography (ICH) or of whole body water using bioimpedance vector analysis (BIVA). K E Bloch, "Impedance and inductance monitoring of cardiac output. Principles and practice of intensive card medicine," 1998; A Piccoli, G Pittoni, E Facco, E Favaro, L Pillon, "Relationship between central venous pressure and bioimpedance vector analysis in critically ill patients" (see comments), Crit Care Med, 28(1): 132–7 (2000); F G Spinale, H D Reines, M C Cook, F A Crawford, "Noninvasive estimation of extravascular lung water using bioimpedance," J Surg Res, 47(6):535–40 (1989). There are not other ways to easily know when excessive extravascular lung or extravascular tissue fluid exists as a result of excessive intravascular volume or as a result of lung or tissue injury. By using measures of extravascular water such as ICH or BIVA, these conditions of excessive intravascular volume versus lung or tissue injury may be distinguished. Situations in which noninvasive CVP was normal or low and extravascular lung or tissue water were high would indicate a state of lung or tissue injury such as adult respiratory distress syndrome or sepsis. Cases in which CVP was high and extravascular lung or tissue water were also high represent a case in which excessive intravascular volume would be deemed as potentially part of the cause. Combining noninvasive CVP with ICH or BIVA with or without the other methods set forth herein to determine optimal preload is useful to provide accurate monitoring tools to optimize central vascular volume.

Additionally, the invention may be used to determine the precise pressure at which the axillary vein occludes. This pressure will reflect CVP, resulting in a non-invasive method to monitor volume status, such as by using the finger(s) as a structure in which volume changes are made since volume changes at this location may occur first in response to axillary vein occlusion, such as with the use of mercury in silastic strain gauges on the finger or photoplethsmography techniques (with motion artifact rejection technology). By monitoring the maximum rate of volume change in the finger, changes in volume produced by axillary vein occlusion may be more easily detected by photoplethsmography. For example, a button transducer may be placed under the finger against the skin of the arm or leg and applied with pressure. However, the use of non-circumferential pressure is considered less preferred.

Another use of non-invasive measurement of CVP according to the present invention is in combination with currently available noninvasive measurements of cardiac output to optimize volume status in conditions such as circulatory shock or congestive heart failure.

Advantageously, the invention may be used in further and additional medical contexts than simply as a substitute for invasive CVP measurement. That is, in some contexts CVP measurement may be desired but invasive CVP would not have been ordered because of the relative risks and disadvantages. By removing the risks and disadvantages of an invasive procedure, the invention makes CVP measurement possible in circumstances where previously it had been desired but would not have been conducted. For example, a noninvasive method or device according to the invention may be used on more patients earlier in their care. Such increased CVP measurement makes possible improvements in patient outcome.

Some examples and experimentation follow for appreciating features of the invention, but the invention is not limited thereto.

EXAMPLE 1

It was observed that previously it had been shown that pressure within the axillary vein of the upper extremity is nearly equal to that of CVP at the level of the superior vena cava and right atrium. It further was observed that previously it had been demonstrated that intraluminal activity vein pressure can be accurately estimated from pressures obtained with pressure cuffs applied to the upper arm, which surround the axillary vein. It was theorized as follows. When applying sufficient pressure over the axillary vein, it occludes preventing venous return. With arterial flow still constant, the forearm swells at a rate proportional to the arterial inflow. The resultant change in forearm volume can be accurately monitored with several types of plethysmography. Rather than calculate the value of forearm swelling, it was proposed that the forearm volume will increase beyond a critical threshold (approximately 0.5% volume) when the axillary vein is occluded. As a result, it should be possible to obtain the occlusion pressure of the axillary vein by monitoring the rate of volume changes in the forearm or calf. This pressure should be highly correlative if not identical to that of CVP.

This was tested by an experimental set-up in which plethysmography with mercury in silastic strain gauges (Hokanson EC-4) was used to measure changes in forearm volume. The strain gauge was placed around the greatest circumference of the forearm. To accurately determine the pressure applied directly over the vein, a pediatric endotracheal (ET) tube with a water manometer was placed offer the axillary vein under the blood pressure cuff, with an initial balloon pressure of 30 cm $H_2O$ (22.1 mmn Hg). The output from the blood pressure cuff was connected to a pressure transducer placed at the level of the right atrium. To eliminate the hand circulation, a wrist cuff was inflated to 140 mm Hg. The pressure transducer and plesythmograph were connected to an AR-6 SIMUTRACE (a multi channel physiologic recording instrument) with a thermal processed paper that gives black and white recording. The subject was placed on a tilt table, which was changed from head up 90° (standing) to head down 30°.

Figure 7A:
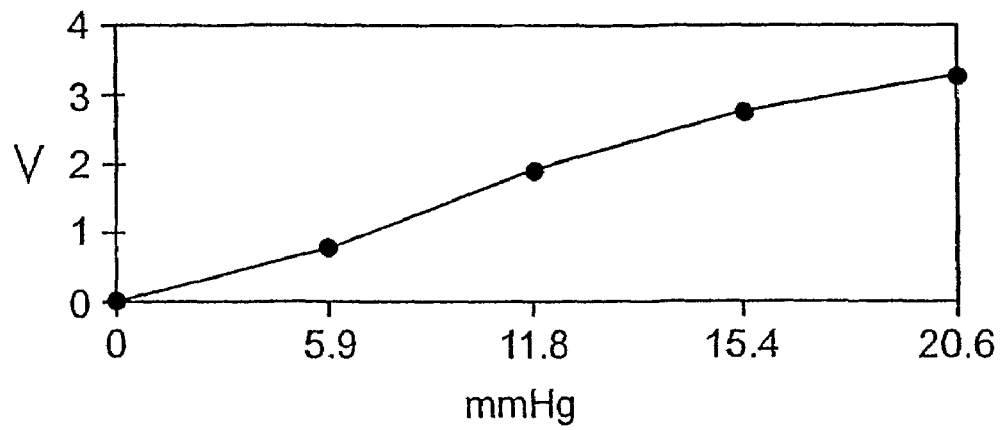
FIGS. 7A–7I are graphs demonstrating cuff pressure/forearm volume changes on a human subjected to various tilts and maneuvers.
Figure 7B:
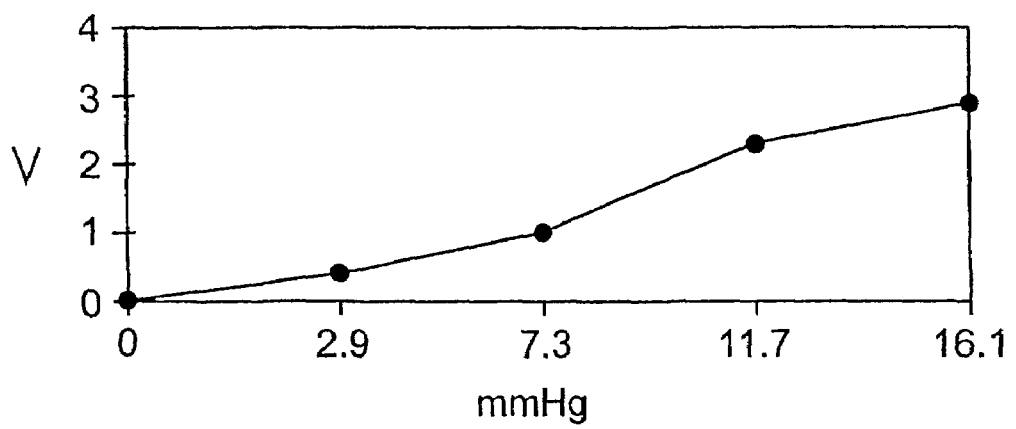
Figure 7C:
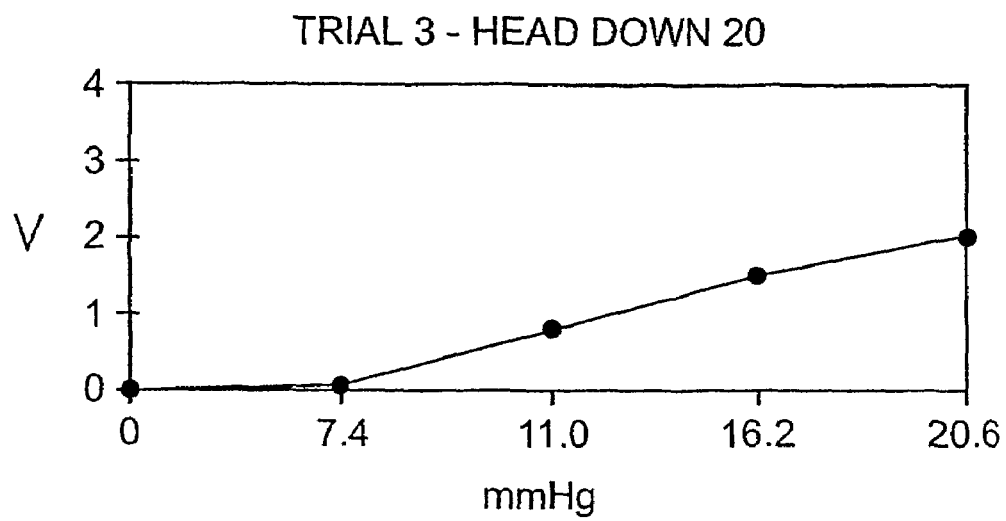

The results were as follows. In trials 1 to 3 (see FIGS. 7A–7C), three positions were used (head up 30°, supine, and head down 20°) to alter CVP, while determining the changes in pressure needed to occlude the axillary vein. The sensitivity of the EC4 was set at 5%, so that a change of one volt corresponded to a forearm volume of 0.5%. V on the figures means the voltage reading on the EC4 plethysmograph which correlates to the changes in the forearm volume. Trials 1 through 3 clearly show an increase in forearm volume (V) which increases with the pressure of the blood pressure cuff. These trials also show that with increasing CVP (from head up 30° to head down 20°) a greater cuff pressure was needed to occlude the axillary vein. At a head up 30° tilt, a pressure of 5.9 mm Hg caused a 0.8 V deflection, while 11.0 mm Hg were required for the same 0.8 V deflection with the head down 20° tilts.

Next, the Valsalva maneuver was tested and demonstrated a similar concept. As the CVP increased during a vasalva maneuver, the forearm volume (V) increased in all three positions. This data suggests that this method is sensitive to changes in CVP.

Figure 7D:
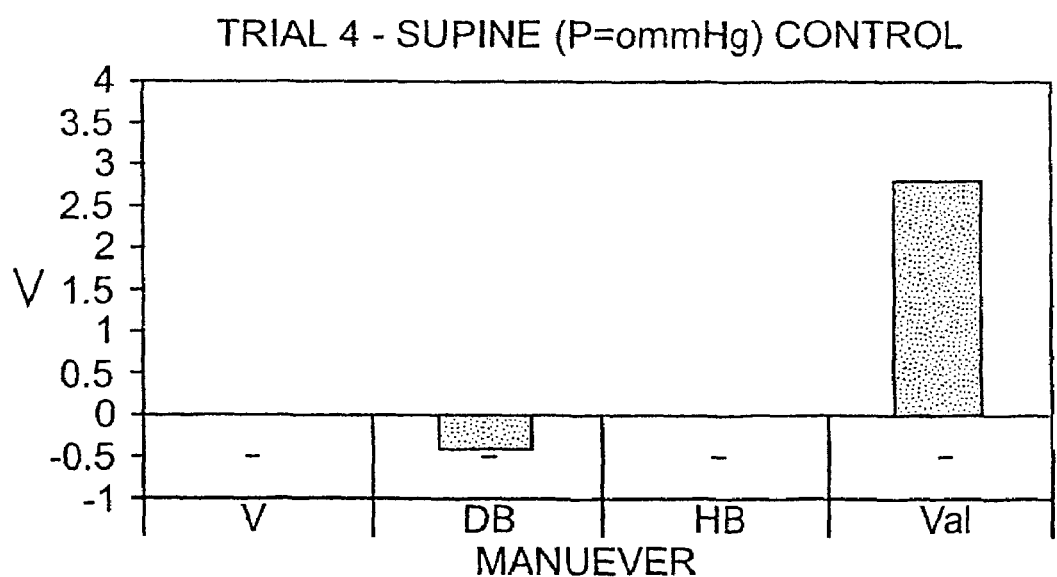
Figure 7E:
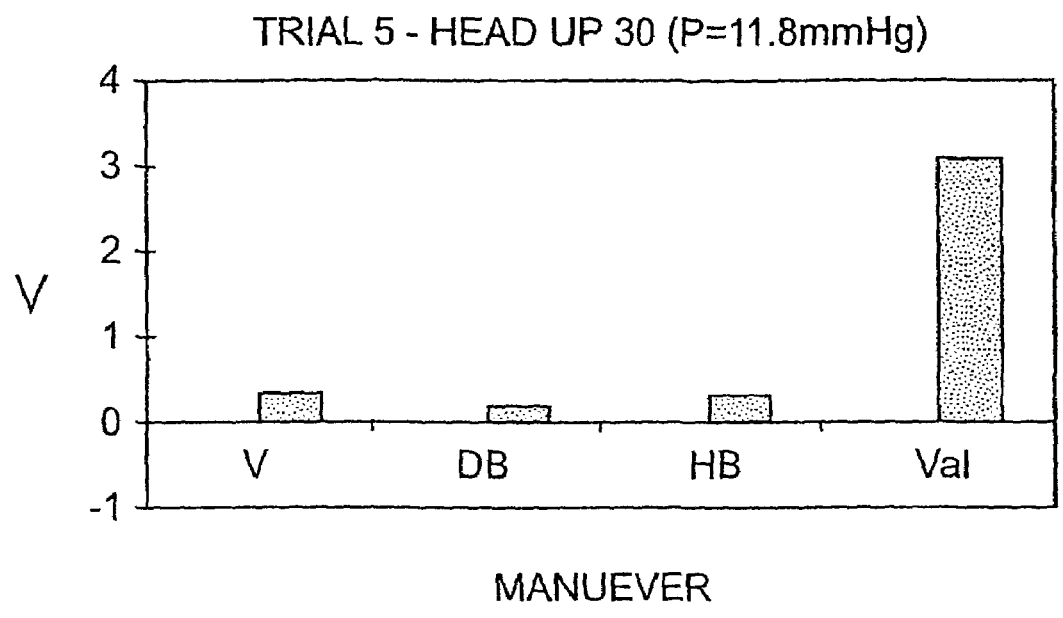
Figure 7F:
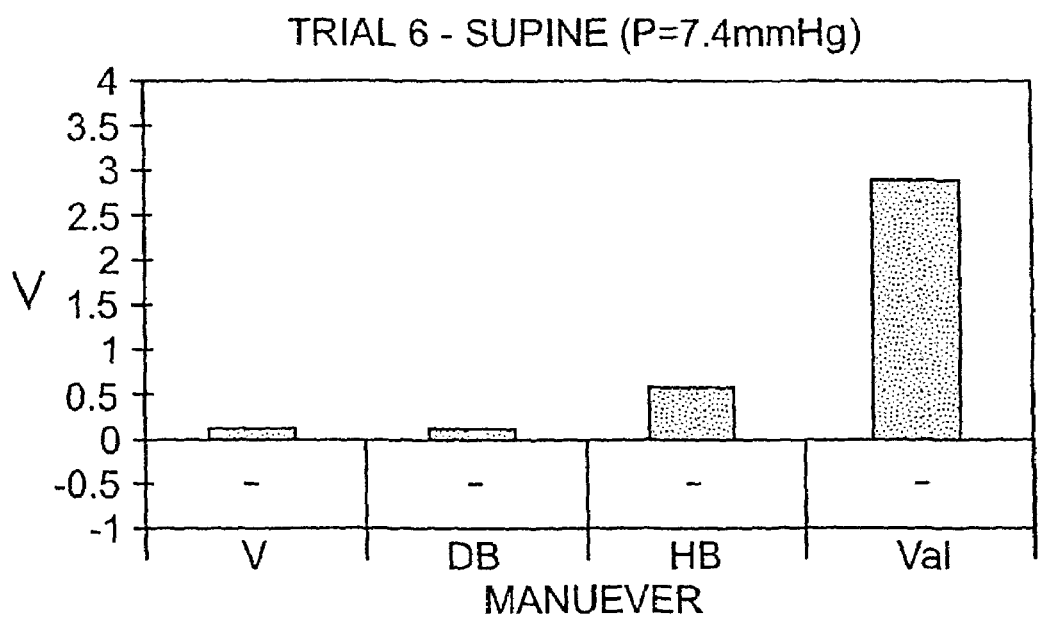
Figure 7G:
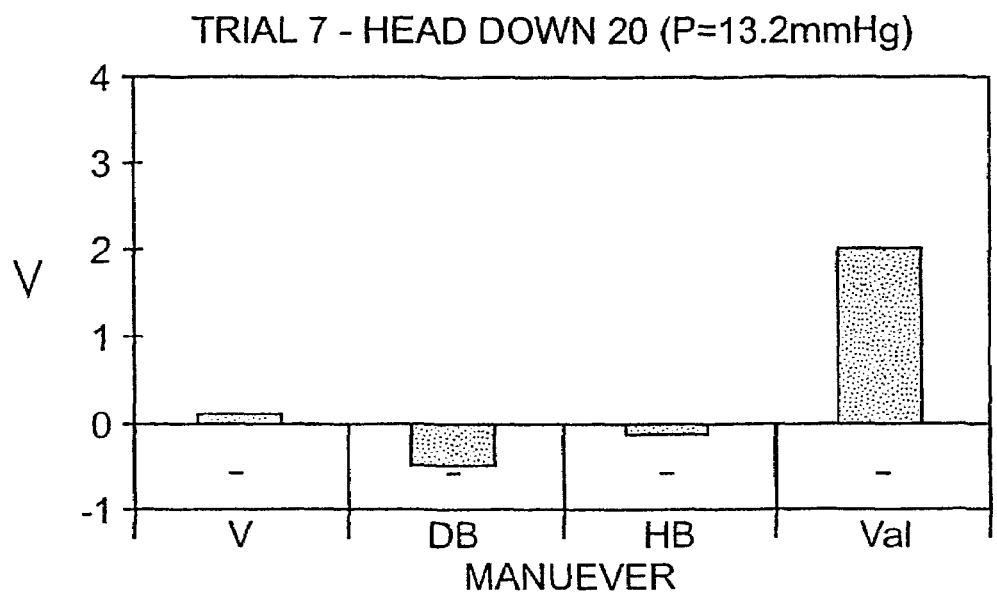

In trials 4 to 7 (see FIGS. 7D–7G), three positions were used (head up 30°, supine, and head down 20°) to establish varying baseline CVPS. At a constant cuff pressure (P), changes in forearm volume (V) were measured following various maneuvers (deep breathing (DB), holding breath with an open glottis (HB), and valsalva (Val)). Trial 4 (FIG. 7D) was supine, wrist=140 mm Hg, speed=10 min/s, ET=30 cm $H_2O$, 5% full scale. Trial 5 (FIG. 7E) was head up 30°, wrist=140 mm Hg, speed=10 mm/s, ET=30 cm $H_2O$, 5% full scale; Trial 6 (FIG. 7F) was supine, wrist=140 mm Hg, speed=10 mm/s, ET=30 cm $H_2O$, 5% full scale; Trial 7 (FIG. 7G) was head down 20°, wrist=140 mm Hg, speed=10 mm/s, ET=30 cm $H_2O$, 5% full scale. On FIGS. 7A–7G, V=volume at constant pressure without any maneuvers.

Trials 4 through 7 (see FIGS. 7D–7G) clearly show that changes in CVP cause a concomitant change in forearm volume. In all three positions, deep breathing (decrease in CVP) caused a decrease in forearm volume relative to the control (V). Similarly, a valsalva maneuver (increase in CVP) caused a drastic increase in forearm volume. Trials 6 and 7 (FIGS. 7F–7G) demonstrate that a valsalva maneuver causes a smaller change in forearm volume when CVP is higher (head down 20°).

Figure 7H:
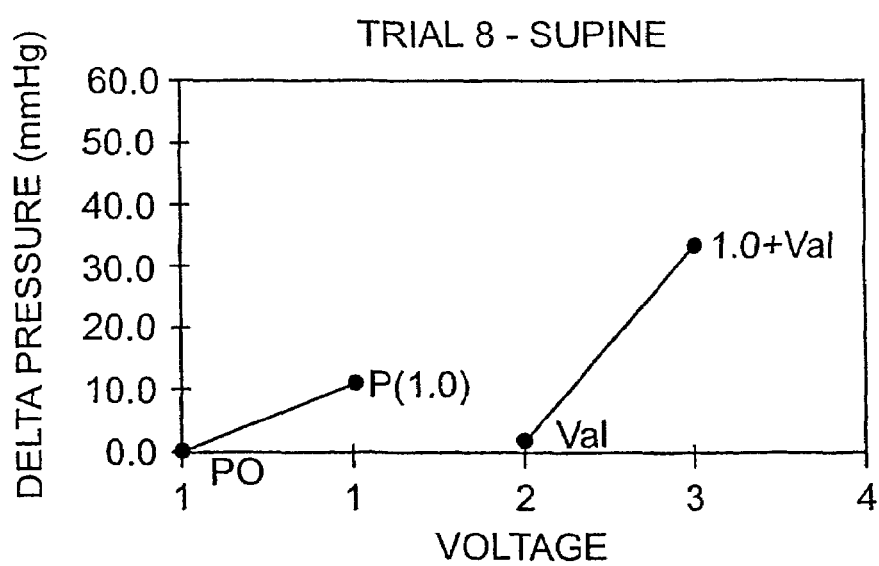
Figure 7I:
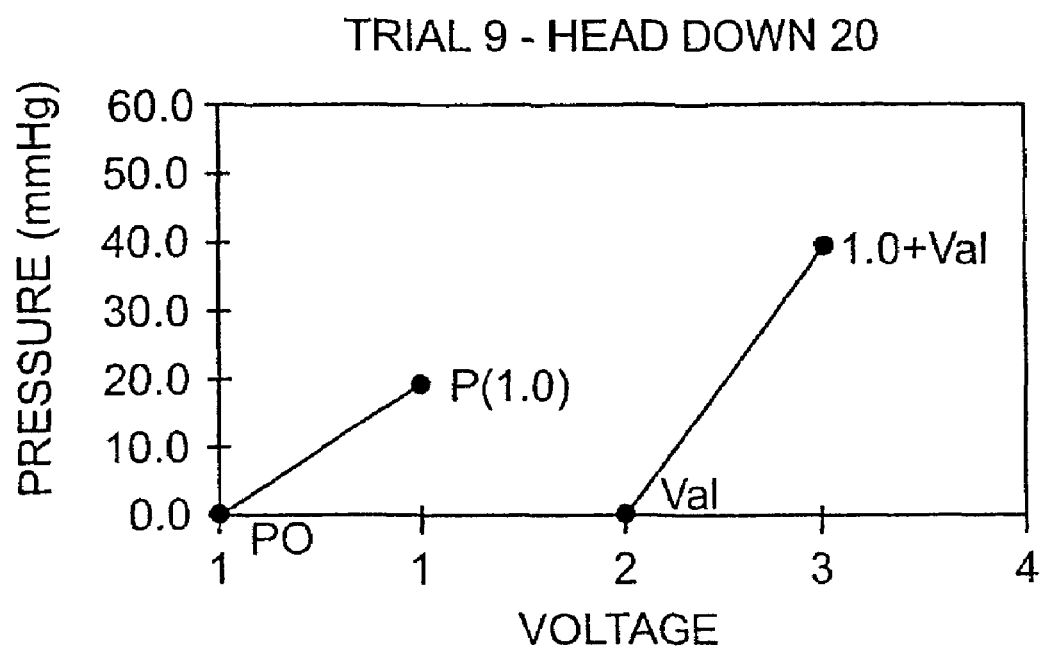

For trials 8 and 9 (see FIGS. 7H–7I), two positions were used (supine, and head down 20°) to establish varying baseline CVPs. Enough pressure was applied to the cuff to attain a change in forearm volume corresponding to one volt. The pressure was then released, and forearm volume was allowed to equilibrate. A valsalva maneuver was performed until forearm volume changed 2.0 V and this state was maintained. Pressure was then applied to the cuff in order to cause a change in forearm volume from 2.0V to 3.0V. The protocol for trials 8–9 was: 1–1.0V threshold (1.0); 2—release pressure; 3—valsalva and maintain at 2.0V (Val); 4–1.0V threshold+valsalva (1.0+Val). Trial 8 (FIG. 7H) was supine, wrist=140 mm Hg; speed=10 mm/s; ET=30 cm $H_2O$; 5% full scale. Trial 9 (FIG. 7I) was head down 20°, wrist=140 mm Hg; speed=10 mm/s; ET=30 cm $H_2O$; 5% full scale. Trials 8 and 9 (FIGS. 7H–7I) clearly show that a larger change in pressure is needed to produce the threshold change in forearm volume (Δ=1.0V) when CVP is increased during valsalva. In trial 8 (FIG. 7H), a pressure of 11.0 mm Hg was required to raise forearm volume from 0–1.0V, while 30.1 mm Hg were needed during valsalva (increased CVP).

These trials also show that an increased baseline CVP (head down 20°) required an even greater change in cuff pressure to elicit a 1.0V change in forearm volume. Only 11.0 mm Hg were required to change forearm volume by 1.0V in the supine position, while 19.9 mm Hg were needed when the head was tilted down 20° (increased CVP). Similarly, 30.1 mm Hg caused a one-volt shift during valsalva when supine, compared to 39.7 mm Hg with the head down tilt.

The data of FIGS. 7A–7I provide evidence that a threshold/critical change in forearm volume is sensitive to changes in CVP. This includes even negative pressure changes. Also, the data show that increasing or decreasing pressures were required to occlude the axillary vein as CVP increased or decreased respectively in response to tilting. Additionally, the data show that these pressures can be accurately quantitated and are within the expected clinical ranges of CVP changes in response to tilting and other maneuvers performed as reported above.

Also, the results of FIGS. 7A–7I show that a noninvasive method of measuring CVP may be a medically sound alternative to direct intravenous measurement of this variable. When combined with a noninvasive cardiac output measurement and derived stroke volume, this noninvasive CVP measurement will help in optimizing the volume status during medical and surgical emergencies and resuscitation. The device will also decrease the need for invasive instrumentation of patients in the intensive care unit setting while aiding in their hemodynamic management. The device also can be seen to be useful in the office or clinic setting for optimal management of such diseases as congestive heart failure or chronic renal failure.

EXAMPLE 2

Figure 4:
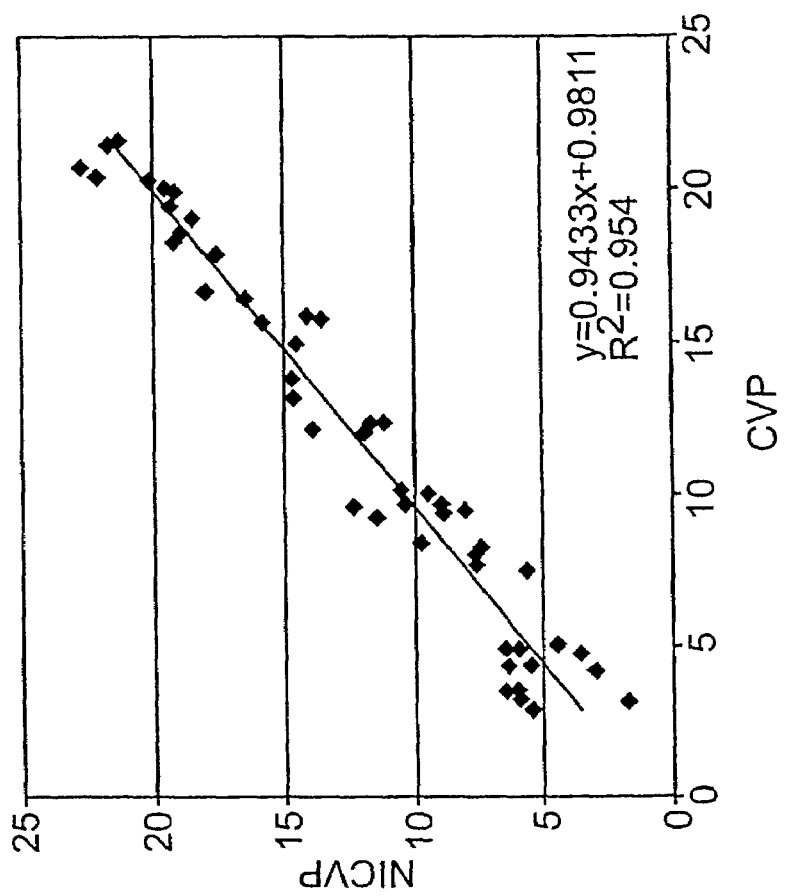
FIG. 4 is a graphical comparison of noninvasive CVP (NICVP) versus invasive CVP.

14 human patients were undergoing invasive monitoring of CVP as part of their routine care. From each patient, simultaneously to taking of invasively measured CVP, non-invasive CVP was taken from the upper extremity using a system according to FIG. 1 herein. Data from these 14 subjects (four readings from each subject) are depicted in FIG. 4. In this series noninvasive CVP was taken from the upper extremity and is compared to the invasively measured CVP. Notably, the correlation is over 0.9 (specifically, 0.97). In no instance would the values have differed to the magnitude that different patient management would have been indicated for the noninvasively measured CVP versus the invasively measured CVP.

EXAMPLE 3

Figure 3:
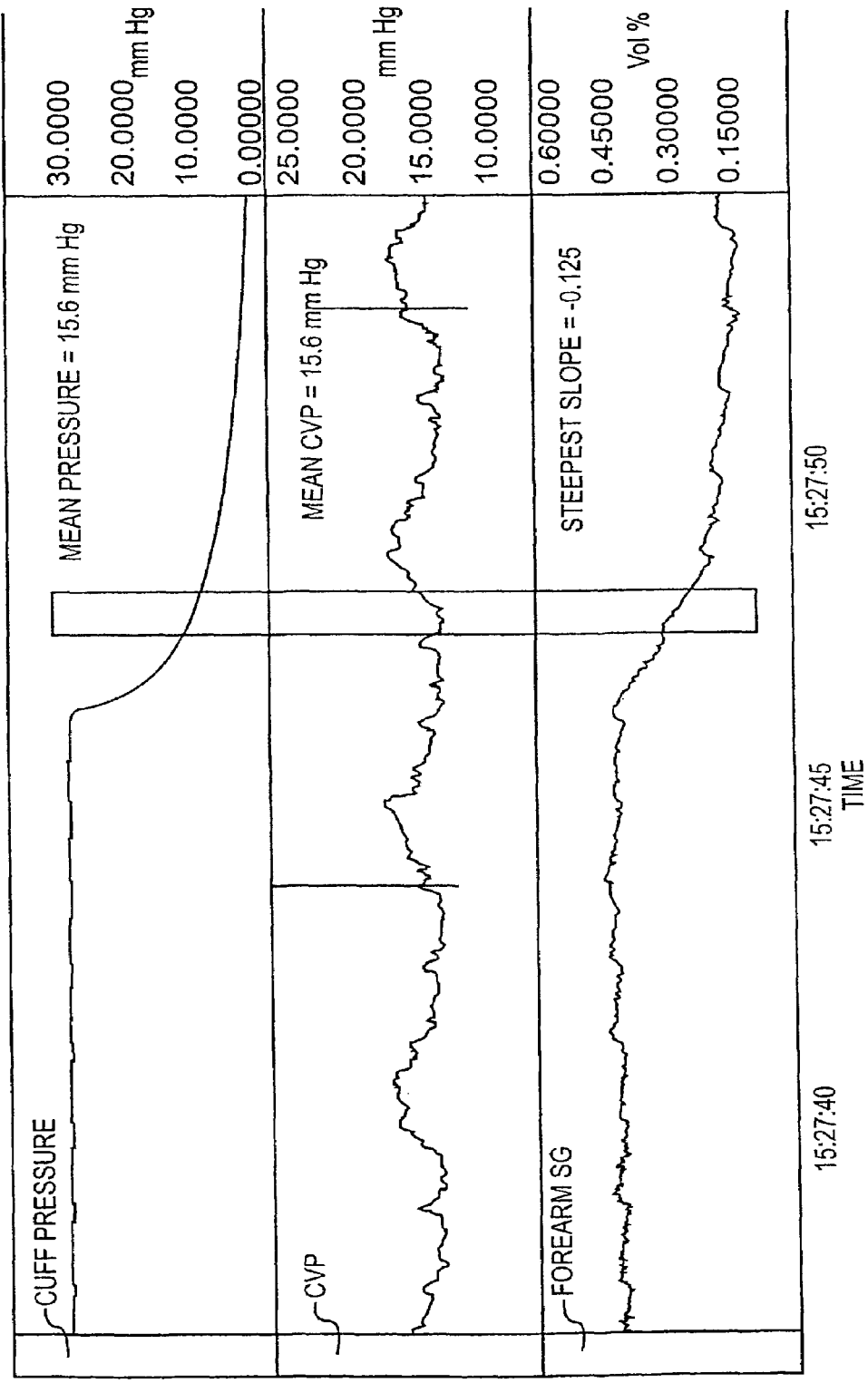
FIG. 3 is a graphical detail during cuff deflation, with the derivative of the strain-gauge slope being the point of maximal flow through the vein and hence pressure within the vein or mean CVP.

FIG. 3 is a detailed analysis of the recording from FIG. 2 during deflation of the vascular cuff. The steepest portion of the slope (derivative) was located. The cuff pressure at this time was noted. In this case it was exactly the same as the mean CVP noted during the time indicated between the two solid bars in the CVP tracing.

EXAMPLE 4

Baseline (BL) inspiration for a patient was observed and recorded, as shown in FIG. 5. Deep inspiration (DB) by a patient also was observed, as shown in FIG. 5. FIG. 5 shows relative decrease in volume noted on deep inspiration as measured by a mercury-in-Silastic strain gauge.

While the invention has been described in terms of its preferred embodiments, those skilled in the art will recognize that the invention can be practiced with modification within the spirit and scope of the appended claims.

We claim:

1. A method for non-invasively determining and optimizing Central Venous Pressure (CVP) comprising the steps of:
   applying a controllable pressure to a vein of interest at a non-distal point of a patient;
   taking pressure and volume measurements from the patient to generate data points;
   plotting intravascular measurements based on the data points as pressure and volume change curves;
   determining from the pressure and volume and change curves an overall slope of the volume change curve and a maximum slope of the volume change curve; and
   determining the CVP based on pressure at the volume change curve maximum slope.

2. The method of claim 1, including the step of absolutely determining central vascular pressure.

3. The method of claim 1, wherein the step of applying a controllable pressure includes inflating and/or deflating a vascular cuff surrounding an extremity upper part.

4. The method of claim 1, wherein the step of applying a controllable pressure includes inflating and/or deflating a vascular cuff surrounding an extremity upper part and further including the step of determining the rate of venous volume change upon deflation of said cuff.

5. The method of claim 1, wherein the step of applying a controllable pressure includes inflating and/or deflating a vascular cuff surrounding an extremity upper part and further including the step of determining the rate of venous volume change upon inflation of the vascular cuff.

6. The method of claim 1, wherein the step of applying a controllable pressure includes inflating and/or deflating a vascular cuff surrounding an extremity upper part and further including the step of determining the threshold of venous volume change upon deflation of the vascular cuff.

7. The method of claim 1, including the step of measuring pressure for a large vein.

8. The method of claim 1, wherein the step of including the step of wherein the step of applying a controllable pressure includes surrounding an upper extremity with an inflatable cuff, and where the method further includes making the volume and pressure measurements while inflating the cuff.

9. The method of claim 8, wherein the inflatable cuff is electrically and pneumatically connected to a programmed cuff inflator device.

10. The method of claim 9, wherein a computer processor receives pressure measurements from the inflatable cuff.

11. The method of claim 10, wherein a volume sensitive detector sends information to the computer processor via a signal amplifier.

12. The method of claim 1, further including the step of non-invasively detecting volume sensitive data for a distal part of an extremity by operating a volume sensitive detector selected from the group consisting of a mercury-in-silastic strain gauge, a bioimpedance device, a photo device, a plethysmography device, a laser Doppler device and a spectroscopic volume detection device.

13. The method of claim 1, wherein the steps of plotting intravascular measurements, determining an overall slope of the volume change curve and a maximum slope of the volume change curve and determining the CVP are performed by a computer system comprising an analogue-digital converter and a data acquisition system.

14. The method of claim 1, further including the step of determining whether intraabdominal pressure is elevated by determining pressure in large leg veins.

15. The method of claim 1, wherein the overall slope of the volume change curve is related to right ventricular compliance and venous return, which changes can be used to optimize a patient's volume status.

16. The method of claim 1, wherein changes in the overall slope of the volume change curve are related to ventricular compliance and venous return, which changes can be used to optimize a patient's volume status.

17. The method of claim 1, further including the steps of titrating fluid resuscitation and/or fluid therapy to maintain a CVP level, and titrating positive end-expiratory pressure (PEEP), to an effect on CVP to optimize both PEEP and CVP.

18. The method of claim 17, wherein fluid therapy titration based on a magnitude of non-invasively determined volume changes during deep inspiration.

19. The method of claim 1, further including the step of monitoring non-invasively determined central venous pressure along with non-invasive measures of cardiac output to indentify an optimized relationship between central venous pressure and cardiac output.

20. The method of claim 19, wherein the measure of cardiac output are selected from the group consisting of carbon dioxide rebreathing, Doppler, bioimpedance and arterial waveform analysis.

21. The method of claim 1, further including the step of:
monitoring non-invasive measures of extravascular lung water along with central venous pressure to differentiate lung injury from fluid excess and/or titrate fluid therapy, and/or differentiate total body fluid excess.

22. The method of claim 21, further including the step of applying a non-invasive measure of extravascular lung water or of extravascular water, selected from the group consisting of impedance cardiography (ICH) data and bioimpedance vector analysis (BIVA) data.

23. The method of claim 1, wherein the step of including the step of wherein the step of applying a controllable pressure includes placing an occluding cuff on an ankle and/or a wrist.

24. The method of claim 23, wherein pressure monitoring is provided by a sensor between the cuff and skin overlying the vessel being monitored.

25. A method of non-invasively determining Central Venous Pressure (CVP) comprising the steps of:
making an identified pressure measurement during a cuff inflation and/or deflation procedure; and
subtracting from the pressure measurement a baseline cuff pressure, to determine CVP according to CVP~ $P_{max\ slope} - P_0$, where $P_0$ is a measured initial pre-inflation pressure in an inflatable vascular cuff applied at a non-distal part of a patient and $P_{max\ slope}$ is a measured pressure at a maximally sloping part of a curve consisting of data points (x,y), with x being a volume variable and y being time.

26. The method of claim 25, wherein variable x is controlled by using voltage used in inflating the vascular cuff.

27. The method of claim 25, including pressure monitoring by providing a sensor between the cuff and skin overlying a vessel being monitored.

28. A system for non-invasively determining Central Venous Pressure (CVP) comprising:
a inflatable cuff for applying a controllable pressure to a vein of interest at a non-distal point of a patient;
a data processing system;
a cuff inflator receiving control instructions from and sending pressure data to the data processing system, the cuff inflator controlling the inflatable cuff in response to control instructions from the data processing system;
a non-invasive volume sensitive detector attached to the patient and sending volume data to the data processing system, said volume data varying in response to pressure applied by the inflatable cuff;
said data processing system plotting intravascular measurements based on the data points as pressure and volume change curves, determining from the pressure and volume and change curves an overall slope of the volume change curve and a maximum slope of the volume change curve, and determining the CVP based on pressure at the volume change curve maximum slope.

29. The system of claim 28, wherein the inflatable cuff is sized for surrounding an extremity in an upper region.

30. The system of claim 28, wherein the data processing system comprises an analogue-digital converter and a data acquisition system.

31. The system of claim 28, further including at least one additional occluding cuff, the additional occluding cuff sized to an ankle and/or a wrist.

32. The system of claim 28, wherein the non-invasive volume sensitive detector is selected from the group consisting of a mercury-in-silastic strain gauge, a bioimpedance device, a photo device, a plethysmov..raphy device, a laser Doppler device and a spectroscopic volume detection device.

33. The system of claim 28, including a pressure monitoring sensor on the inflatable cuff and adapted to be placed between the inflatable cuff and skin overlying a vessel being monitored.

* * * * *